(12) United States Patent
Sykes

(10) Patent No.: US 7,248,970 B2
(45) Date of Patent: Jul. 24, 2007

(54) FORENSIC AND GENEALOGICAL TEST

(75) Inventor: Bryan Clifford Sykes, Oxfordshire (GB)

(73) Assignee: Oxford Ancestors Limited, Kidlington, Oxfordshire (GB)

( * ) Notice: Subject to any disclaimer, the term of this patent is extended or adjusted under 35 U.S.C. 154(b) by 0 days.

(21) Appl. No.: 10/453,194

(22) Filed: Jun. 2, 2003

(65) Prior Publication Data

US 2003/0207314 A1 Nov. 6, 2003

Related U.S. Application Data

(63) Continuation of application No. 09/490,460, filed on Jan. 25, 2000, now abandoned.

(30) Foreign Application Priority Data

Jan. 25, 1999 (GB) .................................. 9901596.8

(51) Int. Cl.
*G01N 33/48* (2006.01)
(52) U.S. Cl. .................... 702/19; 702/20; 707/102; 435/6; 436/501; 536/23.1
(58) Field of Classification Search ................ 702/19, 702/20; 707/102; 435/6; 436/501; 536/23.1
See application file for complete search history.

(56) References Cited

U.S. PATENT DOCUMENTS 6,277,567 B1 * 8/2001 Graziosi ........................ 435/6

FOREIGN PATENT DOCUMENTS

| EP | 0382261 | 8/1990 |
| WO | WO 95/27077 | 10/1995 |

OTHER PUBLICATIONS

Dipierri et al. (Human Biology 1998, vol. 70 No. 6 pp. 1001-1010).*
Caglia et al. (International Journal of Legal Medicine 1998, vol. 111, pp. 142-146).*
Jobling et al. (International Journal of Legal Medicine 1997, vol. 110, pp. 118-124).*
Paoli et al., "Correlations of Quantitative Chromosomal Heteromorphisms and Classic Genetic Markers to Demogeographic Data in Garfagnana Valley (Tuscany, Italy)"; *Human Biology* (1997) 69(1) pp. 11-29.
Guglielmino et al., "The genetic structure of a province as revealed by surnames and HLA genes: potential utility in transplantation policy"; *Ann. Hum. Genet.* (1996) 60 pp. 221-229.
Search Report under Section 17, GB Patent Application No. 9901596.8 (Nov. 4, 1999) 1 page.

* cited by examiner

*Primary Examiner*—Mary K. Zeman
(74) *Attorney, Agent, or Firm*—Fish & Richardson P.C.

(57) ABSTRACT

A method is provided for determining the probable surname of a male from a sample of his tissue or DNA, wherein the haplotype of his sample is compared with a database, the database containing information which correlates Y chromosome haplotypes to given surnames.

7 Claims, No Drawings

FORENSIC AND GENEALOGICAL TEST

RELATED APPLICATION INFORMATION

This application is a continuation of U.S. application Ser. No. 09/490,460, filed Jan. 25, 2000 now abandoned, which claims priority to United Kingdom application serial no. 9901596.8, filed Jan. 25, 1999.

The present invention relates to a method of forensic and genealogical analysis.

Analysis of the structure of DNA may be carried out at a number of different levels, such as at the level of sequence analysis, or at the levels of restriction fragment distribution and microsatellite DNA analysis. Such analysis allows a DNA sample to be matched with an individual from whom the sample was derived, to a high degree of accuracy.

WO95/27077 discloses a Y chromosome minisatellite region which may be suitable for forensic male-specific identification (or exclusion), along with genealogical applications.

Common forensic applications of DNA analysis allow DNA taken from a number of suspects, for example, to be compared with a DNA sample derived from the scene of a crime. Y chromosome DNA samples are especially useful in cases of heterosexual rape, as the male-derived DNA (in the form of the Y chromosome DNA) can be more easily distinguished from the female victim's DNA than autosomally derived DNA. In this way, a comparison of suspect DNA and the sample allows specific individuals to be matched or excluded. Similarly, as the Y chromosome is passed from father to son, parentage may be checked via Y chromosome comparison.

At present, applications of Y chromosome analysis are generally limited to specific families or specific sample comparisons. The present invention sets out to advance the application of Y chromosome analysis.

In a first aspect, the present invention provides a method for determining the probable surname of a male from a sample of his tissue or DNA, wherein the haplotype of his sample is compared with a database, the database containing information which correlates Y chromosome haplotypes to given surnames.

In a further aspect, there is provided a method for the identification of the probable surname of a male from a tissue sample, comprising the steps of:
  i taking tissue samples from males with the same surname;
  ii conducting an analysis of the haplotype of the Y chromosome of such individuals;
  iii correlating the surname with features of the haplotype;
  iv repeating steps i-iii, to provide a database containing information about the relationship between different surnames and haplotype features;
  v determining the haplotype of a sample derived from a man with an unknown surname; and
  vi comparing the haplotype obtained in (v) with the database in (iv), in order to identify the surname of the man from whom the sample was derived.

The present invention uses DNA analysis techniques to haplotype the Y chromosome of male human beings with the same surname. We have, surprisingly, discovered that males with a surname in common often share a common Y chromosome haplotype, that is, have a common paternal ancestor. It follows that knowledge of the haplotype of a DNA sample derived from the Y chromosome of an unknown individual can be used to enable a surname to be assigned to the individual. In order for this assignment to occur, the haplotype of the sample must be compared to a database of haplotypes of individuals of known surnames.

The identification of a common paternal ancestor is surprising, as many names are derived from, for example, professions or geographical features which can arise independently in a number of different locations. The name 'Sykes', for example, means spring, stream or boundary ditch (Redmonds, G., 1992, Yorkshire Surname series 2;53-54, G. R. Books, Huddersfield U.K.), and was previously thought to have several independent family origins in West Yorkshire. However, application of the present invention reveals that only one common ancestor of Sykes is likely, with many 'Sykes' individuals having a common specific haplotype. Those Sykes members without the specific haplotype fall into no other discernible group, which does not support the idea of alternative origins, and can be accounted for statistically by average rates of illegitimacy over the last 700 years when the surname was first recorded.

The realisation that males sharing a common surname may have a single (common) paternal ancestor allows the application of Y chromosome haplotyping to forensic analysis. Specifically, identification of the surname of a man via the analysis of the DNA haplotype of his Y chromosome could be used as a primary forensic screen.

For example, in the case of rape, an analysis of tissue (semen) left by the rapist might enable the likely surname of the rapist to be identified. This analysis could be carried out before any specific suspect had been identified. Subsequent detailed DNA analysis would then be used to identify the specific member of the family involved. Such analysis would be impractical if surnames were derived from multiple independent origins, as one would require an informative locus for each independent origin of each surname to make the technique work. In contrast, we have demonstrated that the Y chromosome haplotype of the surname is informative, which provides for other applications.

In another application of the invention, the analysis may be used to identify the names of accident victims. In addition, the methods indicated would be also be useful in primary analysis of paternity and genealogy, such as direct father-son testing.

The identification of common name ancestors by Y chromosome haplotype analysis also allows standard genealogical approaches to be revised. For example, the findings make it possible to establish direct links between families with the same name even when there is no documentary evidence linking the families.

As such, the present invention also relates to a method of genealogical analysis, wherein Y chromosome samples of males with the same surnames are compared, in order to establish putative common ancestry.

Use of primary surname screening requires the generation of a database which links haplotype to surname. The present invention further relates to such a database, wherein the haplotype of the human Y chromosome at certain positions has been correlated with certain surnames.

The invention further relates to a method of producing a database, comprising the steps of:
 i taking tissues samples from a male with the same surname;
 ii conducting an analysis of the haplotype of the Y chromosome of such individuals;
 iii correlating the surname with features of the haplotype; and
 iv repeating steps i-iii, to provide a database containing information about the relationship between different surnames and the haplotype of the Y chromosome.

Further, the invention relates to use of a database as described above in the analysis of a surname of an individual.

Such a database has further uses. For example, the database allows the origin of surnames with slightly different spellings to be compared. Given the single common ancestors of names thought to have multiple origins, it is likely that individuals having names which are very similar may also have a common ancestor. Indeed, it is possible that surnames which vary greatly and which were previously thought to be unrelated have a common genetic origin. The invention, thus, also relates to a method of surname analysis wherein the Y chromosome haplotypes of names which are related phonetically or in their spelling are compared to identify common genetic origins. Such an approach may also be useful in primary forensic screening, wherein the identification of a surname from a sample can be compared not only with Y chromosomes of men with an identical surname, but those with related surnames.

The present invention also has applications in the tracing of ethnic origin and migration. The realisation that Y chromosome DNA analysis can be practically used to assign a common male ancestor allows population movement and ethnicity to be assessed.

It will be appreciated that the surname of a male relates to his family history, and normally (at least in Europe) to his father's surname. However, surnames may be easily changed. Therefore it will be appreciated that the term 'surname', as used herein, relates generally to the familial history of the man involved, and specifically relates to the donor of the Y chromosome which he has received. In addition, it will be appreciated that the surname is used as an indicator of paternity. However, in certain countries, family names may be indicated in different ways. Therefore, the analysis of 'surnames', as discussed above, includes the analysis of other names where this is appropriate.

It will be appreciated that DNA haplotyping techniques for use in the present invention are well known and standard in the art. Reference 6 in the attached Example 1 gives suitable details of the methods used in this analysis. DNA samples for haplotype analysis may be obtained from any suitable tissue sample, such as semen, blood and mouth swabs, or any other suitable source.

The haplotype of a Y-chromosome is the combination of alleles at different loci along the chromosome. The number of haplotypes recognised in a population is a function of the number of loci and the number of alleles at each locus. There is a large and increasing number of loci suitable for haplotype construction. The present invention is thus not limited to haplotypes derived from specific loci, but extends to haplotypes derived from any suitable combination of loci. Indeed, use of many different loci can increase the specificity and applicability of the invention.

The present invention will now be illustrated with reference to the following examples, which are illustrative of the present invention but not binding upon it.

EXAMPLE 1

Since the Mediaeval period it has been common practice for children to take their father's surname. It is also a biological necessity that a son inherit the Y-chromosome of his father. It follows that males sharing the same surname will also inherit the same Y-chromosome. However, this syllogism is valid only if (i) there were a single common surname ancestor, (ii) there has been no subsequent Y-chromosome divergence and (iii) there have been no incidents of non-paternity. As discussed above, in relation to point (i), a single common ancestor has been thought to be unlikely for many surnames. In order to assess the correspondence between surname and Y-chromosome haplotype, a sample of males with the surname Sykes was ascertained from published lists compiled from electoral rolls and other registers (1). From the UK distribution it was clear that by far the highest residential concentrations of Sykes are in the counties of West Yorkshire, Lancashire and Cheshire. This matches the earliest occurrences of the name in the 13th and 14th centuries from the villages of Flockton, Slaithwaite and Saddleworth, close to Huddersfield, West Yorkshire (2). A postal request for a cheek cell sample was sent to 269 male Sykes chosen at random from the three counties. A total of 61 (22.7%) replies were received and DNA successfully extracted. The first was a sample of 185 English Caucasians from all over the country ("English") and the second, to control for abundant local haplotypes, a group of 21 unrelated male neighbours recruited by the Sykes volunteers ("Neighbour"). Y-chromosomes from all three samples were genotyped at four microsatellite loci in common use.

TABLE

| Haplotype | 'Sykes' | 'Neighbour' | 'English' |
|---|---|---|---|
| 4321 | 0 | 9.5 | 0 |
| 4322 | 0 | 9.5 | 4.9 |
| 4432 | 3.8 | 9.5 | 14.1 |
| 4522 | 0 | 14.3 | 11.9 |
| 4532 | 9.4 | 4.8 | 19.5 |
| 4632 | 5.7 | 4.8 | 2.2 |
| 5422 | 5.7 | 4.8 | 1.6 |
| 5423 | 5.7 | 4.8 | 2.2 |
| 5433 | 39.6 | 0 | 0 |
| 5633 | 5.7 | 4.8 | 0 |
| 5732 | 5.7 | 0 | 0 |

Legend

Haplotype frequencies (%) among the three samples. Y-chromosomes were genotyped at the microsatellite loci DYS 19, 390, 391, 393 in a single run on an Applied Biosystems 373 using primers given in (6). Allele sizes in the population were ranked in ascending size order for each locus and haplotypes constructed. Thus haplotype 5433 has allele 5 at DYS 19, allele 4 at DYS 390 and allele 3 at both DYS 391 and DYS 393. Allele 1 at each locus contained 11(DYS19), 20(DYS390), 9(DYS391) and 12 (DYS 393) microsatellite repeats respectively. Additional alleles increased in size by one repeat unit per unit increase in notation. Only haplotypes which exceeded a frequency of 5% in at least one sample are shown in the table.

There is a highly significant association between Y-chromosome haplotype distribution and the 'Sykes' sample ($P_i=1.4\times10^{-10}$)(7) due entirely to haplotype 5433. This haplotype is not encountered in either the 'Neighbour' or 'English' controls and suggests a common paternal ancestor for these males. This is surprising given the general locality category of the name Sykes which means spring, stream or boundary ditch and is thought to have had several origins in Yorkshire (2).

Haplotype 5433 is carried by 39.6% of the 'Sykes' sample. Only 5 (9.4%) of 'Sykes' haplotypes are one mutational step removed from 5433. Assuming a step-wise mutational model (3), this suggests that there has been relatively little divergence on that chromosome since the name first appeared in the Middle Ages. This makes it unlikely that the bulk of other Sykes haplotype are derived from the common 5433 ancestor. It is possible that some non-5433 Sykes Y-chromosomes come from other founders with that name. However, since no other haplotype occurs at a frequency that is significantly different from the two control groups, the third possibility must be entertained; that these are the result of the historical accumulation of non-paternity. By assuming that each non-5433 haplotype has infiltrated the Sykes genealogy as a single event, the average non-paternity rate estimate is 1.3% per generation (8). Surprisingly, there are no reliable figures for current rates with estimates fluctuating between 1.4 and 30%, although most are in the range 2-5% (5).

If other surnames show a similar degree of association, in addition to use in genealogy, testing a larger range of microsatellite loci might allow for the compilation of surname specific haplotypes which could prove valuable as a primary forensic screen in cases, such as rape, where males leave their Y-chromosomes at the scene of crime.

REFERENCES/COMMENTS

1. 'The Burkes Peerage World Book of Sykes' (1997), Marlborough, Wiltshire, UK.
2. Redmonds g. (1992) Yorkshire Surnames Series. 2; 53-54.
3. Kimura, M and Ohta, T. (1978) Proc. Natl. Acad. Sci. USA 75, 2868-2872
4. Sturges C M, Haggett B C (1987). 'Inheritance of English surnames'. (Hawgood Computing, London) p 7.
5. MacIntyre S, Sooman A (1991) Lancet 338; 869-871.
6. de Knijff P et al. (1997) Int. J. Legal. Med. 110; 134-140.
7. Where $P_i$=the probability that the Sykes and the English samples come from the same population/the probability that the Sykes and the English samples come from different populations
8. This estimate assumes that 23 generations have passed since the first common male ancestor

EXAMPLE 2

A number of other surnames were analysed according to the methods outlined in Example 1. Specifically, the names Blencowe, Foden and Redhead were collected and analysed in the same way.

In the case of Blencowe, which has a geographical distribution suggesting a nucleus in the East Midlands in the vicinity of Northamptonshire, 45% of the sample shred the same haplotype (5423 using the nomenclature in Example 1), and a further 20% were one mutational step distant from this haplotype. This suggests a common origin for this surname.

In the case of Foden, which has a geographical distribution suggesting a nucleus in Cheshire, 74% of the sample shared the same haplotype (4532 using the nomenclature in Example 1) and a further 21% were one mutational step distant from this haplotype. This suggests a common origin for the surname.

The surname 'Redhead' has dual geographical distribution in Cumbria and East Anglia (see "The Surname Detective": investigating surname distribution in England", page 42, 1995, C. D Rogers, Publ. Manchester University Press, Oxford Road, Manchester). In the case of Redhead, 50% of the sample shared the same haplotype (4432 using the nomenclature in Example 1) and a further 30% were one mutational step distant from this haplotype. This suggests a common origin for the surname.

The invention claimed is:

1. A method for predicting the surname of a male from a sample of his tissue or DNA, the method comprising:

(a) analyzing the Y chromosomes of a plurality of males having the same surname at a plurality of microsatellite loci to identify the alleles present at a number of microsatellite loci thereby defining a Y chromosome haplotype for each male analyzed;

(b) correlating the surname of the plurality of males with the Y chromosome haplotypes of the plurality of males to define one or more Y chromosome haplotypes correlated with the surname;

(c) repeating steps (a) and (b) by analyzing the Y chromosomes of males with other surnames to provide a database correlating each surname to one or more Y chromosome haplotypes;

(d) analyzing the Y chromosome from a tissue or DNA sample of the male to identify the allele present at a variety of microsatellite loci to define a Y chromosome haplotype for the male; and (e) comparing the Y chromosome haplotype for the male with the haplotypes in the database to predict the surname of the male.

2. The method of claim 1 wherein step (e) comprises identifying a Y-chromosome haplotype in the database that exactly matches the haplotype for the male.

3. The method of claim 1 wherein step (e) comprises identifying a Y-chromosome haplotype in the database that is one mutational step removed from the haplotype for the male.

4. A method for predicting potential surnames of a male from a sample of his tissue or DNA, the method comprising:

(a) analyzing the Y-chromosomes of a plurality of males having the same surname, phonetically related surnames, similarly spelled surnames or having surnames known to have common historical ancestry at a plurality of microsatellite loci to identify the allele present at a number of microsatellite loci;

(b) correlating the surnames of the plurality of males with the Y chromosome haplotypes of the plurality of males to define one or more Y chromosome haplotypes correlated with the surnames;

(c) repeating steps (a) and (b) by analyzing the Y chromosomes of males with other surnames that are not identical, phonetically related or similarly spelled to provide a database correlating surname to one or more Y chromosome haplotypes;

(d) analyzing the Y chromosome of the male to identify the allele present at a variety of microsatellite loci to define a Y chromosome haplotype for the male; and (e) comparing the Y chromosome haplotype for the male with the haplotypes in the database to predict potential surnames of the male.

5. The method of claim 4 wherein step (e) comprises identifying a Y-chromosome hapiotype in the database that exactly matches the haplotype for the male.

6. The method of claim 4 wherein step (f) comprises identifying a Y-chromosome haplotype in the database that is one mutational step removed from the haplotype for the male.

7. The method of claim 1 wherein step (b) comprises identifying the most common Y chromosome baplotype for each surname and step (e) comprises predicting that the male has the surname most commonly associated with the Y chromosome haplotype of the male.

* * * * *